United States Patent [19]
Bosch et al.

[11] Patent Number: 5,822,865
[45] Date of Patent: Oct. 20, 1998

[54] CUTTING PLIERS FOR CUTTING IMPLANT PLATES

[75] Inventors: Martin Bosch, Emmingen-Liptingen; Joachim Pfefferle, Munstertal; Michael Roth, Ebringen; Peter Scheuble, Wasenweiler; Hermann Zeuner, Freiburg, all of Germany

[73] Assignee: MedArtis AG, Basel, Switzerland

[21] Appl. No.: 717,479

[22] Filed: Sep. 20, 1996

[51] Int. Cl.[6] .................................................... B26B 13/08
[52] U.S. Cl. .................................. 30/134; 30/229; 606/72
[58] Field of Search ........................... 30/134, 229, 230; 606/72

[56] References Cited

U.S. PATENT DOCUMENTS 4,602,431  7/1986  Keel ............................................ 30/229

FOREIGN PATENT DOCUMENTS 4308319  6/1994  Germany .

OTHER PUBLICATIONS

Aesculap Brochure, B–192–11, Edition 194/4/1.

*Primary Examiner*—Douglas D. Watts
*Attorney, Agent, or Firm*—Baker & Daniels

[57] ABSTRACT

A cutting pliers for cutting implant plates features two handgrips (10) joined via a hand-grip pivot (11), which handgrips actuate by way of leverage pivots (14) a pliers holding jaw (15) and a pliers punching jaw (16). Formed on the pliers holding jaw (15) are holding pins (19, 20, 21) adapted for entering matching recesses of the implant plates being cut. A cutting device (18) is fashioned on the pliers punching jaw (16). Implant plates of different implant systems, with half-round, burrless cuts, can be cut with said cutting pliers.

15 Claims, 9 Drawing Sheets

FIG. 19

CUTTING PLIERS FOR CUTTING IMPLANT PLATES

BACKGROUND OF THE INVENTION

1. Field of the Invention

The invention relates to pliers for cutting implant plates and more particularly to a plier having a pliers holding jaw that comprises a holding device for holding the implant plate as well as a holding cutting edge, and a pliers punching jaw which possesses a punching cutting edge, the two being joined via a pivot and actuated by means of pliers grips.

2. Description of the Related Art

Known in osteosynthesis are implant systems where implant plates are screwed to a bone of a patient, by means of screws, in order to fix the bone. Depending on the site of such implant plates, different loads are encountered. Therefore, implant plates of different size, thickness and stability are generally used. In the skull area, for example in the region of the forehead, considerably smaller implant plates can be employed than in the middle part of the face or even in the jaw area. The implant plates coordinated with an implant system differ in shape, but have generally the same material thickness, width as well as identical hole dimensions.

A conventional cutting plier for cutting such implant plates is shown on page 14 of the brochure by the firm Aesculap, B-192-11, edition 194/4/1, with the type description LX 153. This cutting plier features two jaws serving to cut implant plates and pivoting with mutual offset about a jaws joint, so that the plier jaws overlap partly in the closed state. The inside edges of the plier jaws facing the other respective plier jaw are fashioned as cutting edges. In closing the cutting plier, the cutting edges slide past each other, shearing off part of an implant plate placed between the cutting edges. Also, one of the two pliers jaws contains a holding pin as well as a holding bow. An eyelet of the implant plate to be cut can be slipped on the holding pin. By swiveling the implant plate about the holding pin, the implant plate can then be slipped under the holding bow, so that the implant plate is [in cutting] safely retained perpendicularly to the cutting plane formed by the cutting edges while being cut.

The prior cutting pliers allow the cutting of implant plates quickly and easily, with no burrs. But a disadvantage of the prior cutting pliers is that in cutting the implant plate, there is a risk that the cut-off implant parts fly off. Such fly-off implant plate parts may damage objects or injure the patient and, generally, are difficult to recover, leaving their whereabouts frequently uncertain. In the worst case, individual implant plate parts may even remain in the patient's body inadvertently.

SUMMARY OF THE INVENTION

Based on this prior art, the objective underlying the invention is to create a cutting plier that allows cutting of implant plates, without involving the risk of fly-off of the severed implant plate parts.

This objective is met in that the pliers holding jaw possesses on a working surface facing the pliers punching jaw a holding profile that comprises the holding cutting edge, spaced from the edge of the working surface of the pliers holding jaw, and which in cutting interacts with a punching profile that is fashioned on a working surface of the pliers punching jaw facing the pliers holding jaw and which comprises the punching cutting edge that complements the holding cutting edge of the holding profile, the cut-off part of the implant plate being after cutting pinched between a clamping section of the holding profile extending laterally beside the holding cutting edge and a clamping section of the punching profile coordinated with said clamping section.

Considering that the cutting edges interacting in cutting are arranged in a center area of the respective working surfaces of the pliers holding jaws and the pliers punching jaws and that the implant plate part to be cut off can be pinched between pliers holding jaw and pliers punching jaw, the implant part to be cut off is during the cutting process and after its completion pinched between the pliers jaws and thereby retained safely. Consequently, the cutting pliers according to the invention does not involve any risk that the cut-off implant plate parts fly off inadvertently.

In a preferred embodiment, a plurality of holding pins are arranged on a ledge extending in the longitudinal direction of the cutting plier on the holding cutting jaw. The holding pins have different dimensions and are coordinated with different implant plates that have different eyelet inside diameters.

This makes it possible to cut with one and the same cutting plier several types of implant plates that differ in shape and dimensions. As a result, only one cutting plier is necessary for several types of implant plates, which reduces the expenditures for the purchase of surgical instruments and the space needs for their storage. Besides, unlike when one cutting pliers each pertains to a specific implant plate type, there is no risk that the treating physician confuses the individual cutting pliers and, to begin with, reaches for an incorrect cutting pliers. Consequently, the cutting pliers according to the invention allows a quick and targeted completion of the work without loss of time.

BRIEF DESCRIPTION OF THE DRAWINGS

Exemplary embodiments of the invention are described more fully hereafter with the aid of the drawings, which show in.

DETAILED DESCRIPTION

Figure 1:
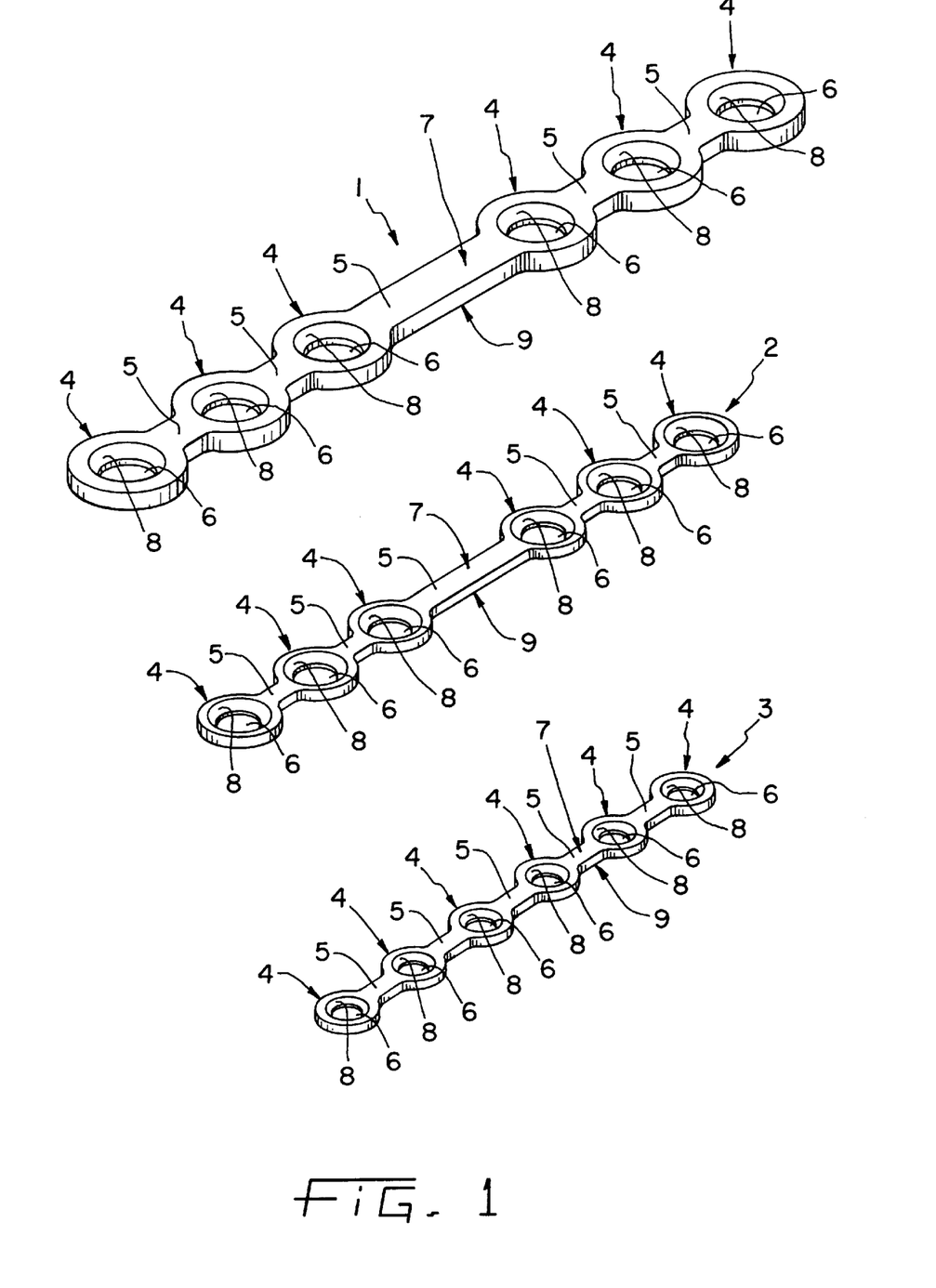
FIG. 1, a perspective view of three implant plates.

FIG. 1 shows a perspective illustration of an implant plate 1 of large material thickness and width, for use in the load-bearing area, an implant plate 2 of medium thickness and width for low loads, and an implant plate 3 of slight material thickness and width for nearly no-load areas. The implant plates 1 through 3 are usually made of titanium and serve in the framework of osteosynthesis to secure bone structures. The implant plates 1 through 3 have eyelets 4 that are joined by webs 5 of different length. The individual webs 5 may differ in length and width. The eyelets 4 have inside openings 6 which toward a screw-in side 7 extend into hole enlargements 8. In fitting one of the implant plates 1 through 3 to the patient's bone, for example the implant plate 2, is first placed on the patient's bone with a bearing face 9 which is opposite the screw-in face 7. The screws to be fastened in the patient's bone are turned in the bone, after sinking appropriate bores in the bone, from the screw-in face 7 through the inside opening 6, until the head of the bone screw engages the hole enlargement 8 and the implant plate 2 pushes down on the patient's bone.

Figure 2:
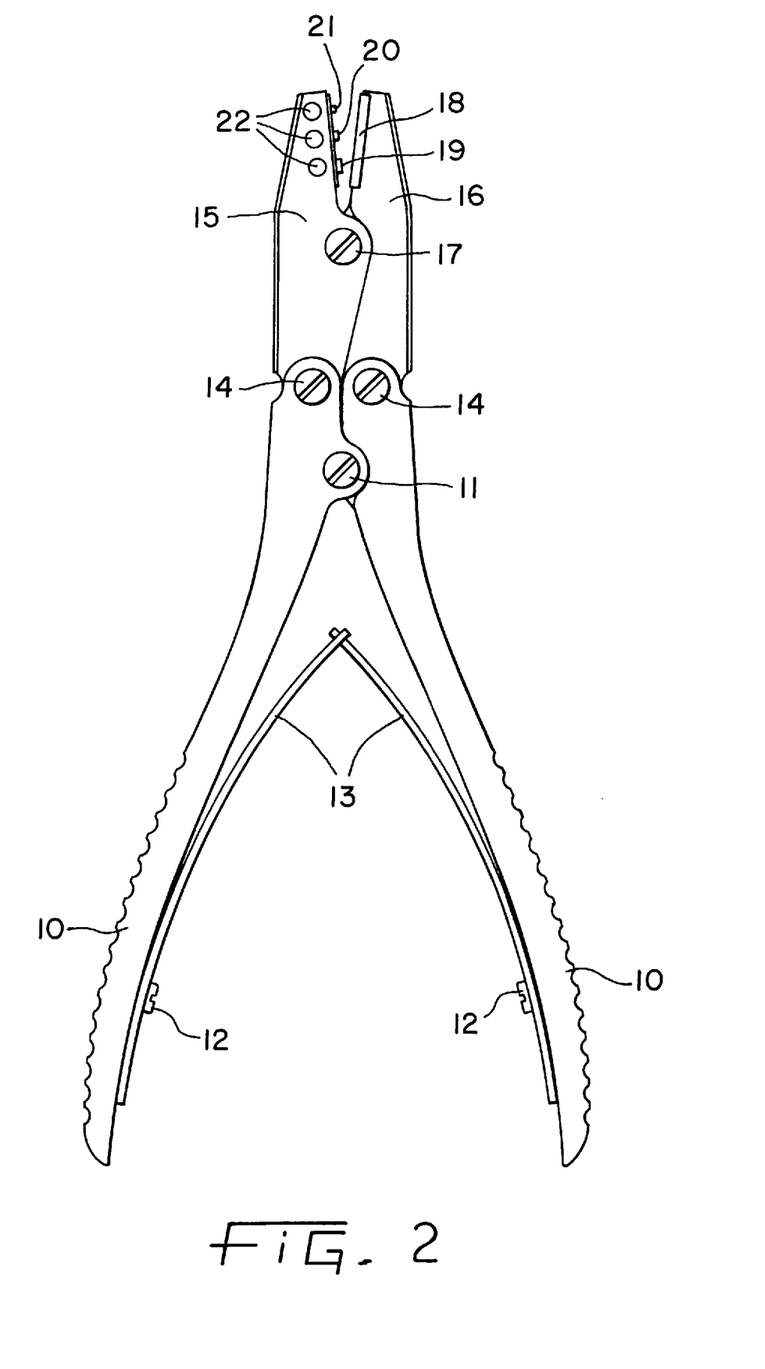
FIG. 2, a side elevational view of a cutting plier according to the invention.

FIG. 2 shows a side elevational view of a cutting plier according to the present invention for cutting the implant plates illustrated in FIG. 1 as well as other implant plates of pertaining implant systems which feature eyelets joined by webs. The cutting plier features two handgrips 10 pivotable about a handgrip pivot 11 joining the handgrips 10. For spreading the handgrips 10, a spring component 13 attached to the handgrips 10 with mounting screws 12 is fitted between the handgrips 10.

A pliers holding jaw 15 and a pliers punching jaw 16 can be actuated with the aid of leverage pivots 14 via the handgrips 10. The pliers holding jaw 15 and the pliers punching jaw 16 are joined by a jaw pivot 17. The pliers punching jaw 16 is equipped with a cutting device 18. Fashioned on the pliers holding jaw 15 are holding pins 19, 20 and 21 for engaging the inside openings 6 in the implant plates 1 through 3. The dimensions of the holding pins 19 through 21 with respect to the diameter of the inside openings 6 are selected so that the implant plates 1 through 3 placed on the holding pins 19 through 21 will have minimal play.

Since the leverage ratio decreases in cutting one of the implant plates 1 through 3 from the jaws pivot 17 to the tip of the pliers holding jaw 15, the holding pin 19 having the largest diameter, for the implant plate 1, is arranged in closest proximity to the jaws pivot 17, while the holding pin 21 with the smallest diameter, for the implant plate 3, is arranged in the area of the tip of the pliers holding jaw 15.

Color codings 22, disposed on the side of the pliers holding jaw 15, are assigned to the holding pins 19 through 21. The color codings 22 allow easy coordination of the implant plates 1 through 3 with the appropriate holding pin 19 through 21.

With the cutting plier according to the invention it is possible to cut implant plates of various implant plate systems. With only one cutting plier needed for the various implant plates 1 through 3, the need to purchase additional surgical instruments is lower and the space needed to store the instruments is reduced. Also, there is no risk that the treating physician during surgery erroneously reaches for a wrong cutting plier that is not appropriate for the specific implant plate system. As opposed thereto, the risk of confusion is reduced when using the cutting plier according to the invention, whereby a swift completion of a procedure, free of disturbing interruptions is possible.

Figure 3:
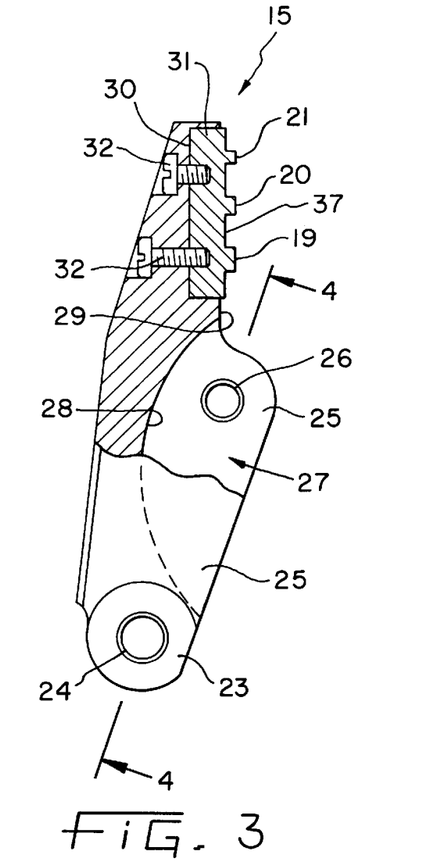
FIG. 3, a partly sectioned side elevational view of a pliers holding jaw of the cutting plier of FIG. 2.

FIG. 3 shows a partly sectioned side elevational view of the pliers holding jaw 15 of the cutting plier of FIG. 2. A leverage joint bearing 24 is fitted in a leverage joint web 23, and a jaw joint bearing 26 is provided in two jaw joint webs 25 arranged sideways on the pliers holding jaw 15. A guide groove 27 with a groove bottom 28, which in the un-sectioned part of the drawing is indicated by dotted line, is located between the jaw joint webs 25. The pliers holding jaw 15 has on its front end opposite the leverage joint web 23 a working face 29 in which a mounting 30 is fashioned, into which a holding insert 31 supporting the holding pins 19, 20 and 21 is inserted. The mounting 30 serves to absorb transverse forces that occur in cutting. The holding insert 31 is fastened in its rear, from the side opposite the working face 29, in the mounting 30 with mounting screws 32.

Figure 4:
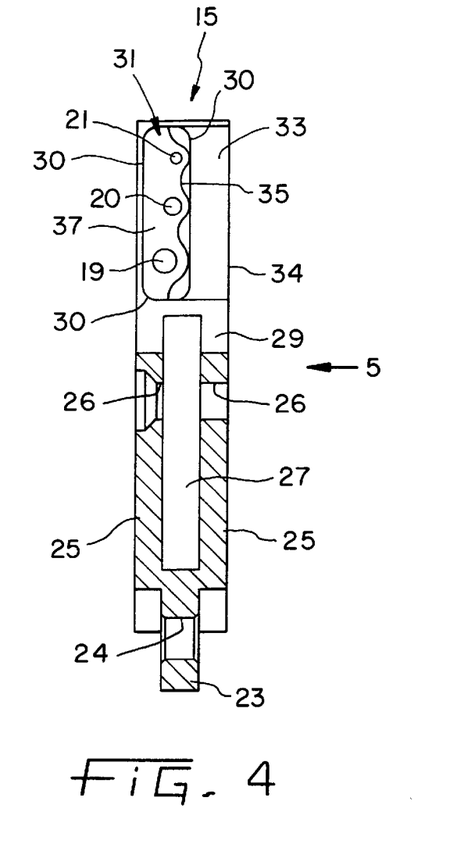
FIG. 4, a cross sectional view of the pliers holding jaw of FIG. 3, along line IV—IV.

FIG. 4 is a cross sectional view of the pliers holding jaw 15 along line IV—IV in FIG. 3. Visible is the leverage joint web 23 and the jaw joint web 25 with the pertaining leverage joint bearing 24 and jaw joint bearings 26. Disposed between the jaw joint webs 25 is the guide groove 27. As can be seen, the holding insert 31 extending in the longitudinal direction of the pliers holding jaw 15 extends in transverse direction approximately across one-half the width of the pliers holding jaw 15. In cross direction, sideways of the holding insert 31, the working face 29 is provided with a recess 33 which toward the edge of the pliers holding jaw 15 is delimited by an outer recess edge 34. The mounting 30 houses the holding insert 31 with the holding pins 19, 20 and 21. The holding insert 31 has a holding cutting edge 35 which in plan view is wavy and follows in the area of the holding pins 19, 20 and 21 the peripheral circle of the eyelets 4 of the implant plates 1, 2 and 3.

When the holding cutting edge 35 is worn or the holding pins 19 through 21 are damaged, the holding cutting edge 35 and the holding pins 19 through 21 can be replaced easily by loosening the screws 32 in FIG. 3 and exchanging the holding insert 31.

Figures 5, 7, 10:
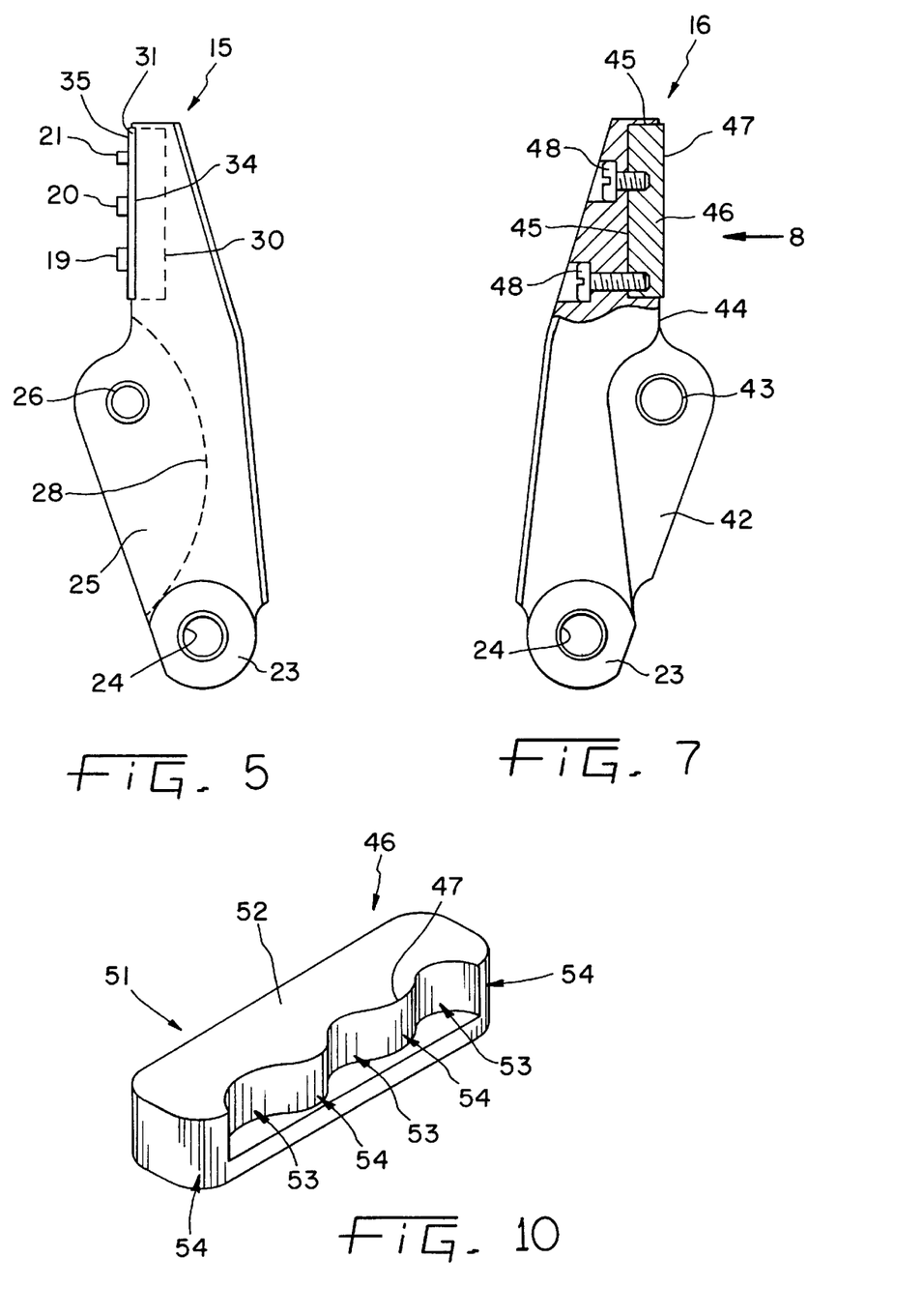
FIG. 5, a side elevational view in the direction of arrow V in FIG. 4.
FIG. 7, a partly sectioned side elevational view of a pliers punching jaw of the cutting plier of FIG. 2.
FIG. 10, a perspective view of the punching insert fitted on the pliers punching jaw illustrated in FIGS. 7 through 9.

For clarification, FIG. 5 shows a further side elevational view of the pliers holding jaw 15 in the direction of arrow V in FIG. 4. Clearly visible is the outer recess edge 34 of recess 33 as well as the holding cutting edge 35 of the holding insert 31. The depth of the recess 33, measured from the holding cutting edge 35 of the holding insert 31, is not appreciably greater than the thickness of the thickest implant plate 1 to be cut. The boundary line of the mounting 30 and the course of the groove bottom 28 are indicated by the dashed line.

Figure 6:
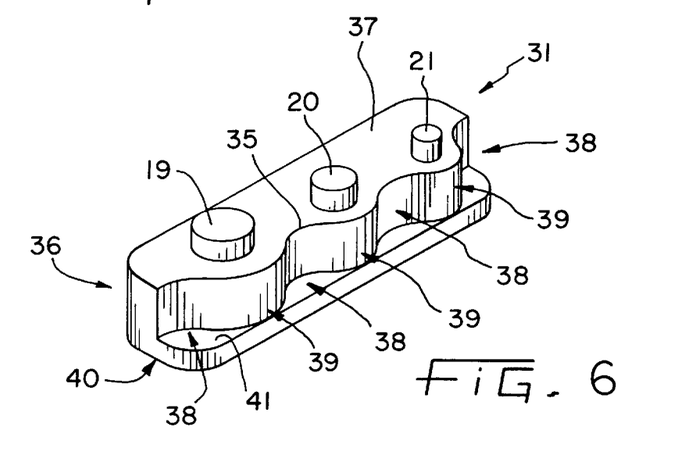
FIG. 6, a perspective view of a holding insert fitted in the pliers holding jaw illustrated in FIGS. 3 through 5.

FIG. 6 represents a perspective view of the holding insert 31. The holding insert 31 possesses a cuboid base 36 with a holding face 37 on which the holding pins 19, 20 and 21 are arranged. To fashion the holding cutting edge 35, bays 38 are recessed in the length side of the base 36. The protruding sidewall parts remaining in the area of the holding pins 19, 20 and 21 are rounded, so that on the respective side wall the bays 38 alternate in the area of the holding pins 19, 20 and 21 with bulges 39. To assure a firm seating of the holding insert 31 in the mounting 30, a pedestal 41 is fashioned in the area of a bearing face 40 opposite the holding face 37, with which pedestal the holding insert 31 can be fitted in the mounting 30 under close fit.

FIG. 7 shows in a partly sectioned side elevational view of the pliers punching jaw 16 of the cutting plier of FIG. 2. Similar to the pliers holding jaw 15 illustrated in FIGS. 3 through 5, the pliers punching jaw 16 is on its one end provided with a leverage joint web 23 in which a leverage joint bearing 24 is fashioned. Also, the pliers punching jaw 16 features a guide web 42 in which a jaw joint bearing 43 matching the jaw joint bearing 25 [sic] of the pliers holding jaw 15 is located. In assembled state, the guide web 42 of the pliers punching jaw 16 engages the guide groove 27 of the pliers holding jaw 15 and serves to prevent distortions of the cutting pliers in cutting.

On the end of the pliers punching jaw 16 opposite the leverage joint web 23, the pliers punching jaw 16 has a working face 44. Fashioned in the working face 44 is a mounting 45 in which a punching insert 46 is fitted. The punching insert 46 is held, on its rear, in the mounting 45 by mounting screws 48. Like the holding insert 31 of the pliers holding jaw 15, the punching insert 46 is provided with a punching cutting edge 47 complementing the holding cutting edge 35. The punching cutting edge 47 allows renewal by exchanging the punching insert 46.

Figure 8:
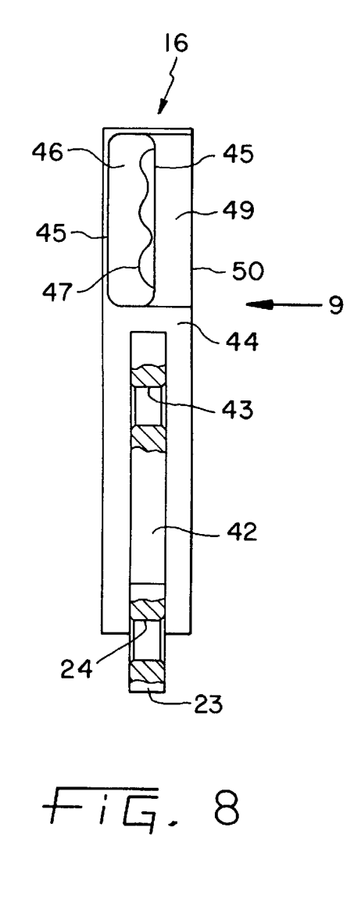
FIG. 8, a partly broken away plan view of the pliers punching jaw of FIG. 7 in the direction of arrow VIII.

FIG. 8 is a plan view of the pliers punching jaw 16, partly broken away in the area of the jaw joint bearing 43 as well as the leverage joint bearing 24, in the direction of arrow VIII in FIG. 7. As shown in FIG. 8, the punching insert 46 is arranged in the longitudinal direction of the pliers punching jaw 16 and extends crosswise approximately over one-half the width of the pliers punching jaw 16. In transverse direction, sideways relative to the punching insert 46, the pliers punching jaw 16 is provided with a recess 49 which outwardly is delimited by an outer recess edge 50. The depth of the recess 49 is so dimensioned that the holding pins 19 through 21 entering the recess 49 do not touch the bottom surface of the recess 49, not even in the closed state of the cutting plier.

Figure 9:
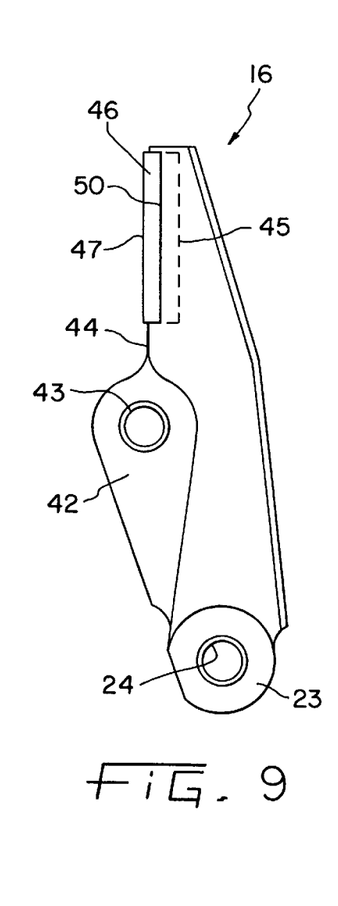
FIG. 9, a side elevational view in the direction of arrow IX in FIG. 8.

FIG. 9 shows for clarification a further side elevational view of the pliers punching jaw 16 along arrow IX in FIG. 8. Distinctly visible is the punching cutting edge 47 of the punching insert 46 as well as the outer recess edge 50 of the pliers punching jaw 16.

The height with which the holding insert 31 protrudes beyond the working face 29 and the height with which the punching insert 46 protrudes out of the working face 44 of the pliers punching jaw 16 are so dimensioned that the holding cutting edge 35 of the pliers holding jaw 15 is parallel to the punching cutting edge 47 of the pliers punching jaw 16 when the punching cutting edge 47 bears on the implant plate 2 of medium material thickness placed on the holding pin 20, so that the implant plates 1 through 3 are being cut substantially full-edge.

FIG. 10 is a perspective illustration of the punching insert 46. The punching insert 46 consists of a cuboid base 51 with a punching face 52. Fashioned on a length side of the base 51 are bays 53 that complement the bulges 39 of the holding insert 31. The bays 53 alternate along the respective side surface with bulges 54 that are complementary to the bays 38 of the holding insert 31 and which, in turn, complement the bays 38 of the holding insert 31. The punching insert 46 fits exactly in the mounting 45.

To cut one of the implant plates 1 through 3, e.g., one of the eyelets 4 of the implant plate 2 is with one's one hand placed on the holding pin 20 assigned to the implant plate 2, while the user's other hand grips the handles 10. To begin with, the implant plate 2 lies generally flat on the holding face 37 of the holding insert 31. Compressing the handgrips 10 causes the pliers punching jaw 16 to approach the pliers holding jaw 15 until the punching face 52 of punching insert 46 makes contact with the screw-in side 7 of the implant plate 2. As the handgrips 10 continue to be compressed, the implant plate 2 assumes a slightly inclined position relative to the pliers holding jaw 15, in which the implant plate 2 bears with its bearing side 9 on the outer recess edge 34 of the pliers holding jaw 15. Since the implant plates 1 through 3 are provided with the hole enlargements 8 and since the dimensions of the holding pins 19 through 21 relative to the diameter of the inside openings 6 are so chosen that the implant plates 1 through 3 placed on the holding pines 19 through 21 possess some play, the eyelets 4 are not deformed due to the slight inclination. As the pliers holding jaw 15 and the pliers punching jaw 16 continue to approach each other, the holding cutting edge 35 and the punching cutting edge 47, to begin digging in uniform fashion into the implant plate 2, creating thereby a rated breaking point. Next, the holding cutting edge 35 of the holding insert 31, along with the punching cutting edge 47 of the punching insert 46, shears the web 5 to be severed off the eyelet 4. In the process, the outer recess edge 50 of the pliers punching jaw 16 forces the implant plate 2 back onto the holding face 37 while the punching cutting edge 47 pushes the part of the implant plate 2 being severed on the bottom surface of the recess 33. With the cutting plier according to the invention, hence, the cutting is carried out by a combined shearing and wedge-action cutting process. Upon completion of the cutting process, the severed part of the implant plate 2 is pinched between the recess 33 and the punching face 52 of punching insert 46, which prevents the severed part of the implant plate 2 from flying off.

The applicational range of these cutting pliers covers implant plates with a thickness ranging from a few tenths of a millimeter to several millimeters. The cutting pliers of the present invention yields a half-round cut free of burrs, without risking fly-off of the cut-off implant plate parts.

To obtain a burrless cut by the combined shearing and wedge-action cutting operation that can be carried out with the cutting plier according to the invention, it is necessary for the material of the implant plate 2 being cut not to have any possibility of escaping the holding cutting edge 35 and the punching cutting edge 47 to free spaces, by elastic deformation during the cutting operation. Thus, the holding cutting edge 35 and the punching cutting edge 47 must for a burrless shearing slide closely past each other. Therefore, it is important for the cutting pliers to possess a sufficient stability against the transverse forces that occur during cutting. As mentioned above, the holding insert 31 and the punching insert 47 are for that purpose each fitted in a mounting 30 and a mounting 45. Also, the guide web 42 entering the guide groove 27 prevents distortion of the cutting pliers while cutting one of the implant plates 1 through 3.

Contributing to a burrless cut is also the fact that the holding cutting edge 35 and the punching cutting edge 47 extend substantially parallel at the start of the cutting operation making contact with one of the implant plates 1 through 3, so that the cutting operation takes place substantially on the full edge. This prevents the material from escaping by elastic deformation from one section of the holding cutting edge 35 and the punching cutting edge 47 with a small clearance between the holding cutting edges 35 and the punching cutting edge 47 toward a section along the holding cutting edge 35 and the punching cutting edge 47 with greater clearance between the holding cutting edge 35 and the punching cutting edge 47, forming there a burr. Also, an even shearing across the width of web 5 is guaranteed thereby.

Lastly, the pattern of the holding cutting edge 35 and the punching cutting edge 47, wavy in plan view and following in the area of the holding pins 19 through 21 the peripheral circle of the eyelets 4 beyond the area of the web 5, contributes also to the absence of burrs in the cutting operation. Due to the sections of the holding cutting edges 35 and the punching cutting edge 47 that follow the peripheral circle of the eyelet 4 beyond the web 5, also the peripheral surface of the eyelet 4 adjacent to the web 5 is kept free of burrs. If a burr forms by sideways escape of the material of the implant plate 1 through 3 on the peripheral surface of the eyelet 4 bordering on the web 5, said burr is removed in cutting by the section of the holding cutting edges 35 and the punching cutting edge 47 that follows the periphery of the eyelets 4 beyond the web 5.

Figure 11:
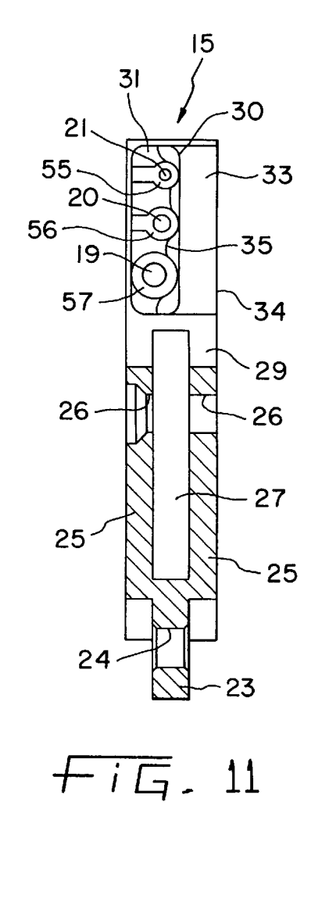
FIG. 11, a plan view of a modified exemplary embodiment of the pliers holding jaw.

FIG. 11 shows a plan view of the pliers holding jaw 15 of a modified embodiment of the cutting plier according to the invention. In this embodiment, the implant plates 1 through 3 can be placed in mountings 55, 56 and 57. The mountings 55 through 57 prevent a turning of the implant plates 1 through 3 about the respective holding pins 19 through 21, thereby assuring that the implant plates 1 through 3 are in cutting transverse to the longitudinal axis of the cutting pliers aligned for a burrless cut. To prevent a deformation of the eyelets 4 of the implant plates 1 through 3, holding pins 19 through 21 are arranged in the mountings 55 through 57. To simplify fabrication, the holding pins 19 through 21 arranged in the mountings 55 through 57 may also be omitted.

Figure 12:
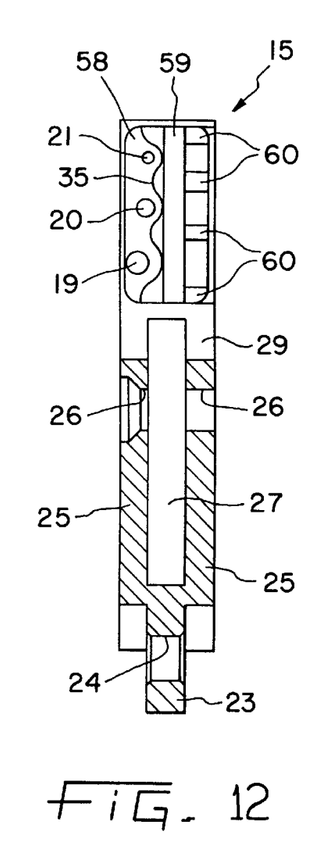
FIG. 12, a plan view of another modified exemplary embodiment of the pliers holding jaw.

FIG. 12 is a partly sectioned plan view of a further modified embodiment of the pliers holding jaw 15 according to the invention. This embodiment features a holding insert 58 which substantially extends across the entire width of the pliers punching jaw 16. One longitudinal half of the holding insert 58 comprises the holding cutting edge 35 with holding pins 19 through 21. Fashioned on the other longitudinal half of the holding insert 58 is a groove 59 extending longitudinally, which borders in cross direction a section provided with alignment ledges 60 extending in transverse direction. The same as the mountings 55 through 57, the alignment ledges 60 ensure the transverse alignment of the implant plates 1 through 3 in cutting, relative to the cutting pliers.

Although not illustrated in FIG. 12, the pliers punching jaw 16 coordinated with the modified exemplary embodiment of the pliers holding jaw 15 complements the holding insert 58 of the pliers holding jaw 15, in order to enable the cutting of the implant plates 1 through 3 and the pinching of the cut-off implant plate parts. More particularly, the punching insert features a ledge that possesses the punching cutting edge 47 and which in cutting the implant plates 1 through 3 enters the groove 59.

Figure 13:
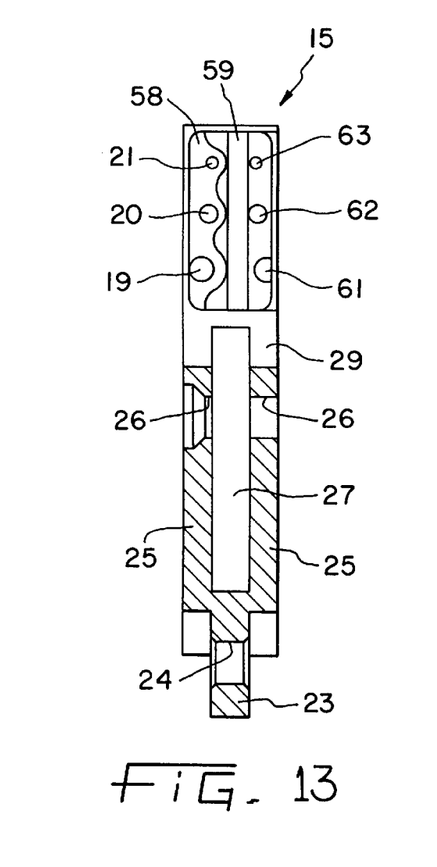
FIG. 13, a plan view of a further modified exemplary embodiment of the pliers holding jaw.

FIG. 13 shows a further exemplary embodiment in which the alignment ledges 60 are replaced by alignment pins 61 through 63 assigned respectively to the holding pins 19 through 21. In this exemplary embodiment, the implant plates 1 through 3 can be placed, for cutting, with their eyelets 4 on the coordinated holding pins 19 through 21 and the alignment pins 61 through 63, whereby they are held securely in cutting.

Similar to the modified exemplary embodiment illustrated in FIG. 12, the pertaining pliers punching jaw 16 is of a design complementing the pliers holding jaw 15 and possesses a ledge that features the punching cutting edge 47 and in cutting enters the groove 59.

Figure 14:
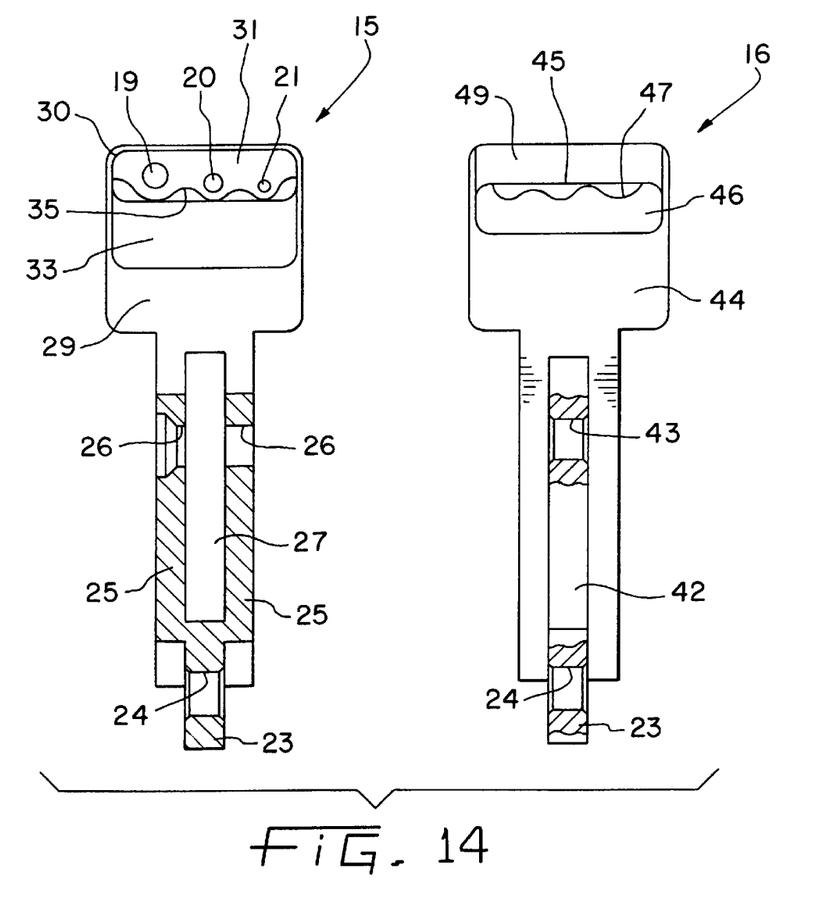
FIG. 14, partly sectioned, two plan views of a modified exemplary embodiment of the pliers holding jaw and the pertaining pliers punching jaws wherein the punching insert and holding insert are aligned each in transverse direction.

Lastly, FIG. 14 shows a modified exemplary embodiment where the holding insert 31 is arranged in the pliers holding jaw 15 and the punching insert 46 in the pliers punching jaw 16, in a direction transverse to the cutting pliers. Such a cutting plier is suited especially for retroactive deburring of previously cut implant plates.

Figure 15:
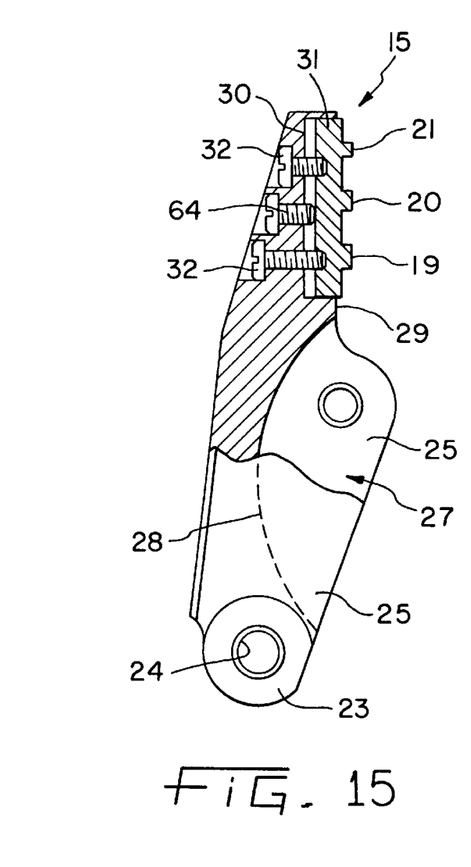
FIG. 15, a partly sectioned side elevational view of an exemplary embodiment of the pliers holding jaw where the level of the punching insert above the working surface is adjustable.
Figure 16:
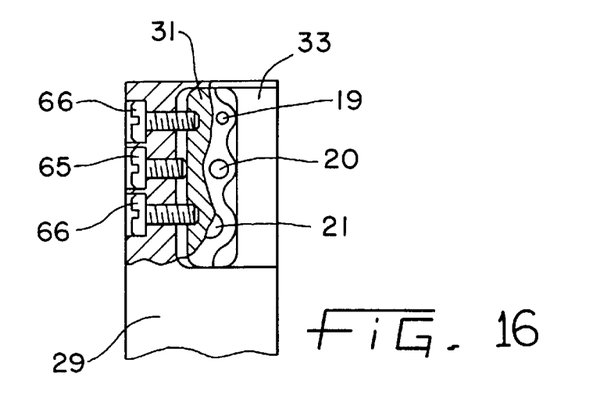
FIG. 16, a partly sectioned plan view of a further exemplary embodiment of the pliers holding jaw where the holding insert is adjustable laterally.

Finally, FIGS. 15 and 16 show modified exemplary embodiments where the holding insert 31 is adjustable by an adjustment screw 64, as illustrated in FIG. 15, as regards the level of insert 31 above the working face 29, or, as shown in FIG. 16, by an adjustment screw 65 and two mounting screws 66 in cross direction. This makes it possible to adjust one and the same cutting plier to implant plates with different dimensions, notably thickness dimensions.

Figure 17:
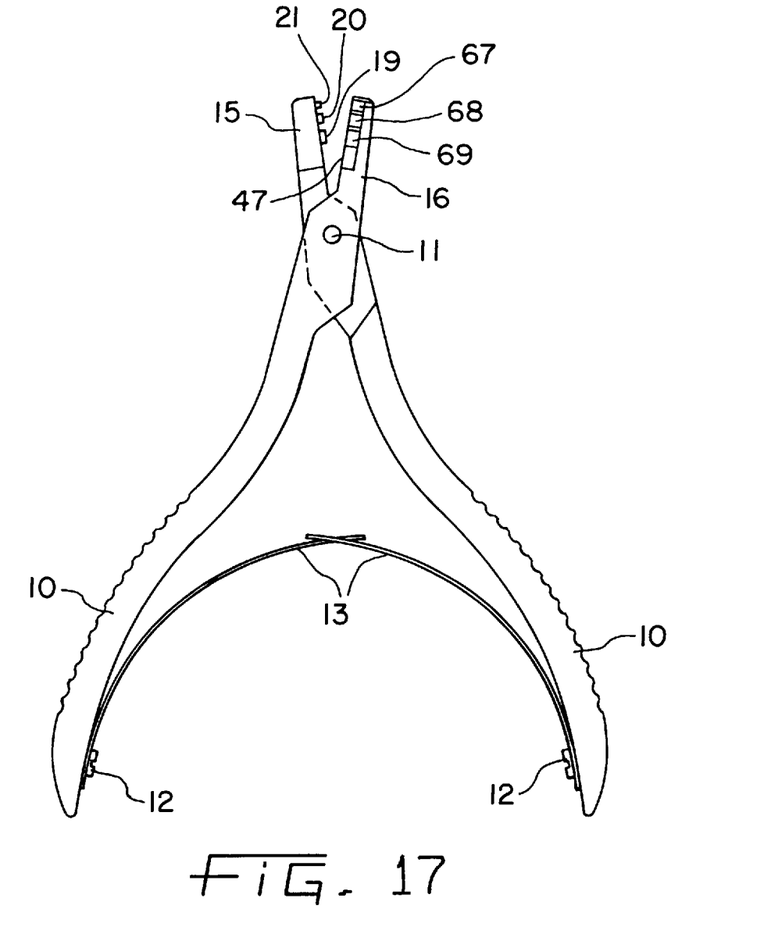
FIG. 17, a modified exemplary embodiment of a cutting plier according to the invention.

Finally, FIG. 17 shows a simplified exemplary embodiment of a cutting plier according to the invention. In this exemplary embodiment, the pliers holding jaw 15 and the pliers punching jaw 16 are joined, after the fashion of a straight plier without leverage, rigidly to a pertaining handgrip 10. As in the exemplary embodiment illustrated in FIG. 2, the pliers holding jaw 15 possesses holding pins 19, 20 and 21 which are coordinated with the implant plates 1, 2 and 3. Fashioned on the cutting jaw 15, in the area of the holding pins 19 through 21, is also the holding cutting edge 35, which sectionally extends along the peripheral circle of the eyelets 4 of the implant plates 1 through 3. The punching cutting edge 47 complementing the holding cutting edge 35 is formed on the punching cutting jaw 16 of bays 67, 68 an 69.

Figure 18:
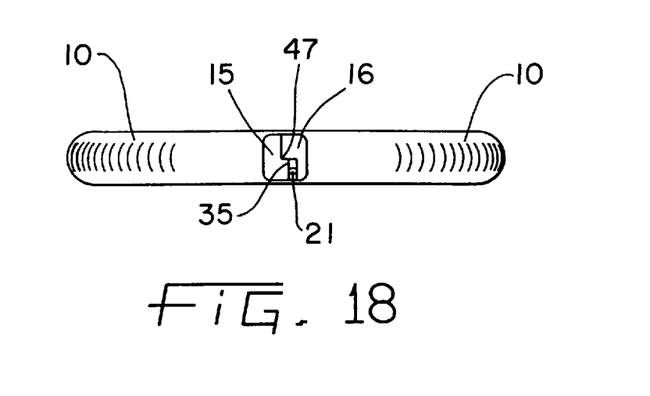
FIG. 18, a front view of the cutting plier of FIG. 17.

FIG. 18 shows a front view of the modified exemplary embodiment of a cutting plier of FIG. 17. The illustration shows the cutting pliers in closed state. Clearly visible is the meshing of the pliers holding jaw 15 and pliers punching jaw 16.

The exemplary embodiment of a cutting plier illustrated in FIG. 17 and 18 requires in cutting a greater expense of force than the exemplary embodiment of a leveraged cutting pliers according to the invention, as illustrated in FIG. 2, and does not possess either its torsional rigidity, whereas this exemplary embodiment is less expensive and easier to manufacture.

Figure 19:
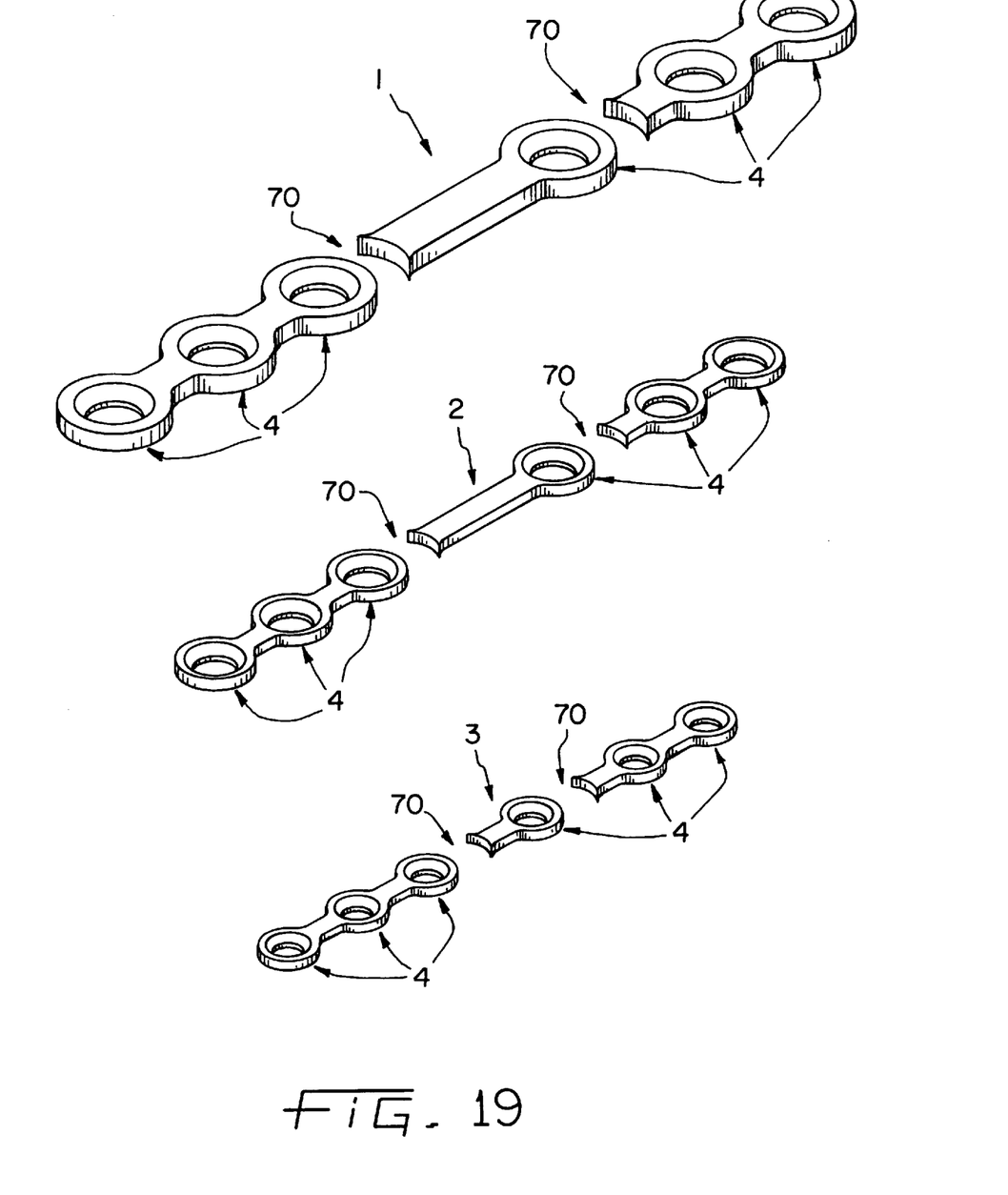
FIG. 19, a perspective view of the implant plates of FIG. 1 in sectioned state.

FIG. 19 shows once again, for clarification, in a perspective view the implant plates 1 through 3 of FIG. 1 in sectioned state. It is clearly evident that a half-round and burrless cut 70 following the peripheral circle of the eyelets 4 can be carried out with the cutting pliers of FIG. 2 or FIG. 17.

We claim:

1. A cutting pliers for cutting implant plates which include eyelets, said cutting pliers comprising:

a holding jaw having an outer edge;

a punching jaw pivotally connected to said holding jaw;

a pair of handles, one of said handles respectively connected to said holding jaw and punching jaw;

said holding jaw including a holding surface for holding a said implant during a cutting operation, said holding surface facing said punching jaw, said holding surface including a holding cutting edge spaced from said outer edge;

said punching jaw including a punching surface, said punching surface including a punching cutting edge which complements said holding cutting edge and which cooperates therewith for effecting a cutting operation;

a recessed pinching portion in said holding jaw located between said holding cutting edge and said outer edge;

said punching jaw including a second pinching portion;

whereby, after a cutting operation, a cut off portion of a said cutting implant is captured between said recessed and second pinching portions.

2. Cutting pliers according to claim 1 wherein said holding cutting edge and the punching cutting edge both include bays and bulges which complement a outside line of the said eyelets of the said implant plates.

3. Cutting pliers according to claim 1 wherein said holding jaw includes a holding insert that extends across substantially one half of said holding surface and having an inside edge which defines said holding cutting edge, said punching jaw including a punching insert having an inside edge for defining said punching cutting edge.

4. Cutting pliers according to claim 3, wherein the holding insert and the punching insert both extend in the longitudinal direction of the cutting pliers.

5. Cutting pliers according to claim 3, wherein the holding insert and the punching insert both extend transversely to the longitudinal direction of the cutting pliers.

6. Cutting pliers according to claim 3 wherein said holding insert is removably mounted on the holding jaw.

7. Cutting pliers according to claim 3 wherein the punching insert is removably mounted on the punching jaw.

8. Cutting pliers according to claim 1, wherein the holding jaw includes a pin on which the eyelets of a said implant plate can be placed.

9. Cutting pliers according to claim 1 wherein said holding jaw includes a plurality of holding pins with different dimensions whereby, the material thickness of a variety of said implant plates is coordinated with said holding pins.

10. Cutting pliers according to claim 9, wherein said recessed pinching portion includes a plurality of alignment pins which are coordinated with said holding pins.

11. Cutting pliers according to claim 8 including a plurality of alignment ledges in said recess pinching portion which extend transversely to the longitudinal axis of the cutting pliers and which are coordinated with the holding pins.

12. Cutting pliers according to claim 9, wherein the holding jaw includes a plurality of mounting cavities into which a said variety of implant plates can be placed.

13. Cutting pliers according to the claim 12 wherein the holding pins are respectively disposed in the respective centers of the mounting cavities.

14. Cutting pliers according to claim 1, wherein said handles are pivotally interconnected and include leveraged pivots for actuating said holding jaw and said punching jaw.

15. Cutting pliers according to claim 1, including a spring mounted between said handles for urging said punching and holding jaws to an open position.

* * * * *